United States Patent
Emir et al.

(10) Patent No.: US 11,828,822 B2
(45) Date of Patent: Nov. 28, 2023

(54) SIMULTANEOUS MULTI-SLICE MRSI USING DENSITY WEIGHTED CONCENTRIC RING ACQUISITION

(71) Applicant: Purdue Research Foundation, West Lafayette, IN (US)

(72) Inventors: Uzay Emir, West Lafayette, IN (US); Mark Chiew, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 47 days.

(21) Appl. No.: 17/607,774

(22) PCT Filed: Apr. 30, 2020

(86) PCT No.: PCT/US2020/030867
§ 371 (c)(1),
(2) Date: Oct. 29, 2021

(87) PCT Pub. No.: WO2020/223567
PCT Pub. Date: Nov. 5, 2020

(65) Prior Publication Data
US 2022/0214414 A1  Jul. 7, 2022

Related U.S. Application Data

(60) Provisional application No. 62/840,975, filed on Apr. 30, 2019.

(51) Int. Cl.
*G01R 33/483* (2006.01)
*A61B 5/055* (2006.01)
(Continued)

(52) U.S. Cl.
CPC .......... *G01R 33/4835* (2013.01); *A61B 5/055* (2013.01); *G01R 33/485* (2013.01); *G01R 33/4824* (2013.01); *G01R 33/4828* (2013.01)

(58) Field of Classification Search
None
See application file for complete search history.

(56) References Cited

U.S. PATENT DOCUMENTS

| | | | |
|---|---|---|---|
| 2014/0225612 A1* | 8/2014 | Polimeni | G01R 33/4835 324/309 |
| 2015/0035531 A1* | 2/2015 | Stemmer | G01R 33/4824 324/309 |

(Continued)

FOREIGN PATENT DOCUMENTS

DE   102018202546 B3   3/2019

OTHER PUBLICATIONS

International Search Report corresponding to International Patent Application No. PCT/US2020/030867, dated Sep. 21, 2020 (6 pages).

(Continued)

*Primary Examiner* — Rodney E Fuller
(74) *Attorney, Agent, or Firm* — Maginot, Moore & Beck LLP

(57) ABSTRACT

A method of performing magnetic resonance spectroscopic imaging (MRSI) measures neurochemical profiles over larger regions non-invasively. The method includes transmitting a multi-slice excitation pulse through tissue, the multi-slice excitation pulse configured to generate multi-slice MRSI signals. The method also includes performing density weighted concentric ring acquisition on the multi-slice MRSI signals. The method further includes receiving the generated multi-slice MRSI signals in a plurality of sensors disposed in various locations around the tissue. Imaging data is reconstructed based on the acquired imaging signals. A representation of the data is displayed.

20 Claims, 14 Drawing Sheets

(51) Int. Cl.
*G01R 33/48* (2006.01)
*G01R 33/485* (2006.01)

(56) References Cited

U.S. PATENT DOCUMENTS

2017/0016972 A1   1/2017   Bhat et al.
2017/0192073 A1   7/2017   Miyazaki et al.
2020/0408863 A1*  12/2020  Liang ................ G01R 33/5615

OTHER PUBLICATIONS

Chiew et al., "Density-weighted concentric rings k-space trajectory for 1H resonance spectroscophic imaging at 7 T," NMR Biomed. (2018) 31:e3838, entire document [online] < http://onlinelibrary.wiley.com/doi/pdf / 10.1002/nbm.3838 >.
Steel et al., "Metabolic-cycled density weighted concentric rings k-space trajectory (DW-CRT) enables high-resolution 1 H magnetic resonance spectroscopic imaging at 3-Tesla," Sci. Rep. 8. 7792 (2018). p. 1, para 1: p. 2, para 1, 3, 5, 6; p. 3, Fig 1 [online] < http:doi.ord/10.1038/s41598-018-26096-y >.

* cited by examiner

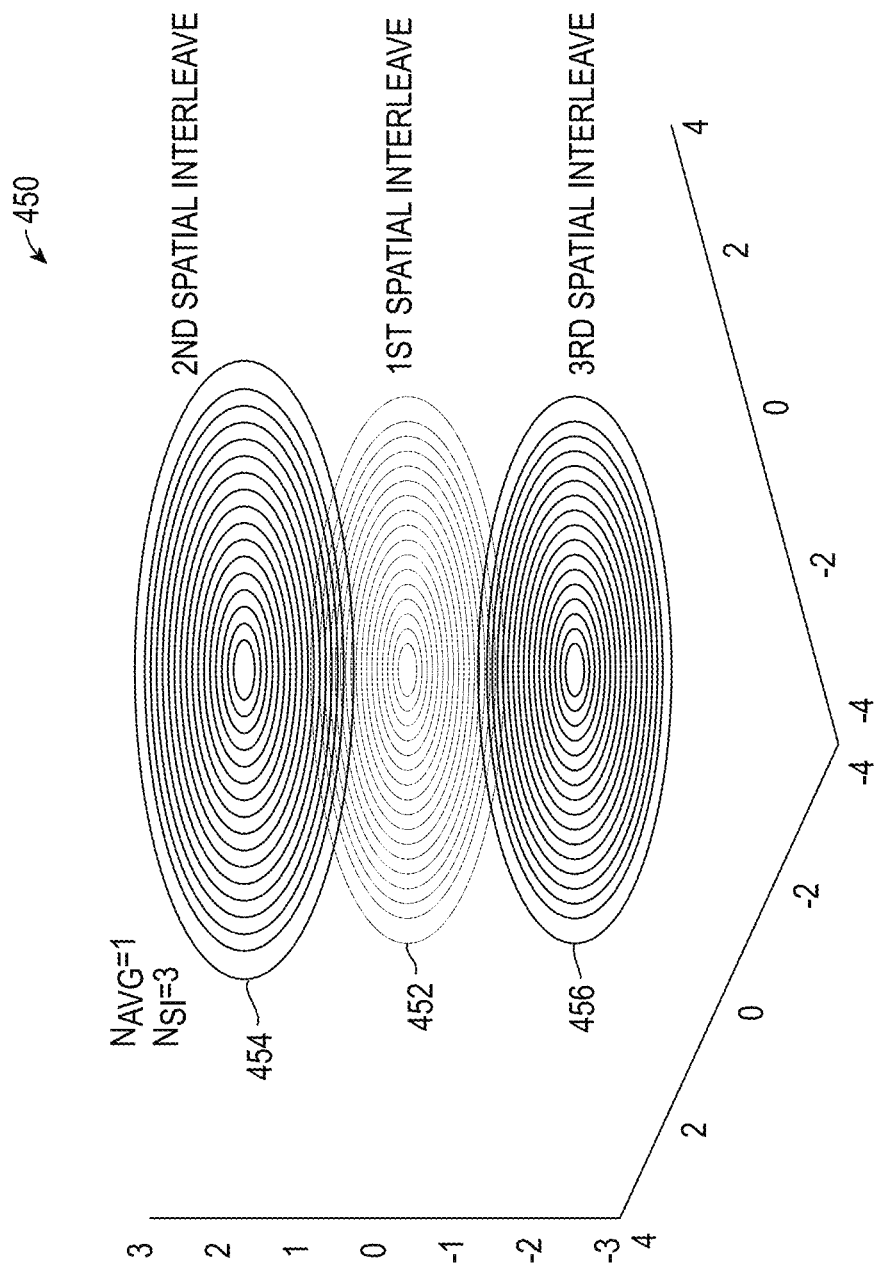

SIMULTANEOUS MULTI-SLICE MRSI USING DENSITY WEIGHTED CONCENTRIC RING ACQUISITION

This application claims the benefit of U.S. Provisional Patent Application Ser. No. 62/840,975, filed Apr. 30, 2019.

GOVERNMENT LICENSE RIGHTS

This invention was made with government support under funding number UL1TR001108, awarded by the National Institute of Health. The government has certain rights in the invention.

FIELD

The present invention relates generally to magnetic resonance spectroscopic imaging (MRSI).

BACKGROUND

Magnetic resonance spectroscopy (MRS) as disclosed herein is a quantitative MR technique that allows neurochemicals to be accurately assayed in vivo in humans. A wide variety of neurochemicals can be detected by MRS, including N-acetylaspartate (NAA), creatine (Cr), choline (Cho), myo-inositol (myo-Ins), and glutamate/glutamine (Glu/Gln). MRS can be used to characterize the progression of neurodegenerative disease (e.g. amyotrophic lateral sclerosis 2 and Parkinsons' disease), conduct non-invasive biopsies to distinguish between types of tumors and address fundamental neuroscience questions. MRS techniques yield information about a single voxel, or single volume element.

An extension of single-voxel (SV) MRS is MRSI, which allows neurochemical profiles to be acquired from multiple voxels simultaneously over substantial regions of the brain. By acquiring multiple voxels simultaneously, MRSI has clear advantages over SV spectroscopy for both research and clinical purposes, but this technique has been hampered by several factors, including relatively long acquisition times, side lobe artifacts, eddy-current-induced artifacts, and tracking B) drifts due to subject motion or thermal fluctuation. In addition, the practicality of MRSI methods is compromised by low concentrations of metabolites relative to water, leading to low signal-to-noise ratios (SNRs) as well as long acquisition times due to spectral and spatial encoding.

There have been several methods proposed to accelerate acquisition duration for MRSI. Some methods relate to the k-space that represents the acquired MRSI data. The k-space is an array of numbers obtained in the MRSI process representing spatial frequencies in the MRS image. A k-space trajectory is the phase and frequency encoding geometry used to acquire the k-space points. The basic k-space trajectory is cartesian, which can be used in echo planar spectroscopic imagine. Other k-space trajectories used to accelerate data acquisition include spiral trajectories, as discussed in Adalsteinsson E, Irarrazabal P, Topp S, Meyer C, Macovski A, Spielman D M, "Volumetric spectroscopic imaging with spiral-based k-space trajectories." *Magn Reson Med* 1998; 39:889-898. Another accelerated trajectory has been demonstrated using the concentric rings trajectory, discussed in Furuyama J K, Wilson N E, Thomas M A, "Spectroscopic imaging using concentrically circular echo-planar trajectories in vivo." *Magn Reson Med* 2012; 67:1515-1522. Several of the parallel imaging methods have been applied to MRSI to accelerate conventional and accelerated k-space trajectories. Recently, a feasibility study was performed to evaluate using CAIPIRINHA to accelerate along three spatial dimensions. This study is discussed in Strasser B, Považan M, Hangel G, et al. "(2+1)D-CAIPIRINHA accelerated MR spectroscopic imaging of the brain at 7T." *Magn Reson Med* 2017; 78:429-440.

While simultaneous multi-slice (SMS) or multi-band (MB) parallel imaging is frequently used in fMRI to accelerate acquisition, functional MRI differs from the MRSI in that it does not perform spectroscopy. Recently, a feasibility study facilitate SMS has been performed to accelerate MRSI acquisition along slice selection direction using EPSI. This study is discussed in Schmidt R, Seginer A, Tal A. "Combining multiband slice selection with consistent k-t-space EPSI for accelerated spectral imaging." *Magnetic Resonance in Medicine* (2019).

However, the usefulness of such multi-band slice MRSI technology has been limited by drawbacks, including long acquisition times, even if the acquisition time is improved over single slice technology. Techniques that reduce acquisition time are often accompanied by significant signal to noise ratio costs. There a need, therefore, for an MRSI technology that overcomes one or more of the issues of the prior art.

SUMMARY

Embodiments disclosed herein feature a multi-slice or multi-band MRSI using density weighted concentric ring trajectory (DW-CRT) acquisition. Sampling the k-space using a density weighted pattern to shape the spatial response function improves side lobe artefacts and signal-to-noise ratio (SNR). In some embodiments, a non-water-suppressed metabolite-cycling is implemented for simultaneous detection of the metabolites and water signals at short echo time (TE=14 ms) using stimulated echo acquisition mode (STEAM) localization. This provides the required information for voxel-wise single-scan frequency, phase, gradient-induced sideband and eddy current correction.

A method of performing magnetic resonance spectroscopic imaging (MRSI) measures neurochemical profiles over larger regions non-invasively. The method includes transmitting a multi-slice excitation pulse through tissue, the multi-slice excitation pulse configured to generate multi-slice MRSI signals. The method further comprises receiving the generated multi-slice MRSI signals in a plurality of sensors disposed in various locations around the tissue. In addition, The MRSI signals are acquired using density weighted concentric ring trajectory acquisition. MRSI image data is reconstructed, and a representation of the imaging data is then displayed and/or stored.

The method described herein alleviates the long acquisition time by acquiring simultaneous multislice (SMS) MRSI. In some embodiments, simultaneous acquisition of water and metabolite images using non-water suppressed acquisition schemes enables correction of the gradient-induced sideband modulations, eddy-current-induced artifact, tracking $B_0$ drifts and motion correction.

In some embodiments, the non-water suppressed SMS MRSI uses density weighted concentric (DW-CRT) k-space trajectory. The DW-CRT k-space trajectory offers significant benefits over cartesian-based trajectories as well as uniformly-weighted CRT trajectories. To this end, DW-CRT has been demonstrated to provide a substantial improvement in SNR and sidelobe signal suppression. Many of the embodiments described herein develop a sensitive method for zoomed, or reduced field of view, high-resolution MRSI.

The above-described features and advantages, as well as others, will become more readily apparent to those of ordinary skill in the art by reference to the following detailed description and accompanying drawings.

BRIEF DESCRIPTION OF THE DRAWINGS

FIG. 5 shows a representation of a three-slice k-space trajectory that may be obtained via the MRSI system of FIG. 1;

FIG. 6b shows an exemplary spatial slice profile corresponding to the multi-slice excitation band of FIG. 6a;

DETAILED DESCRIPTION

Figure 1:
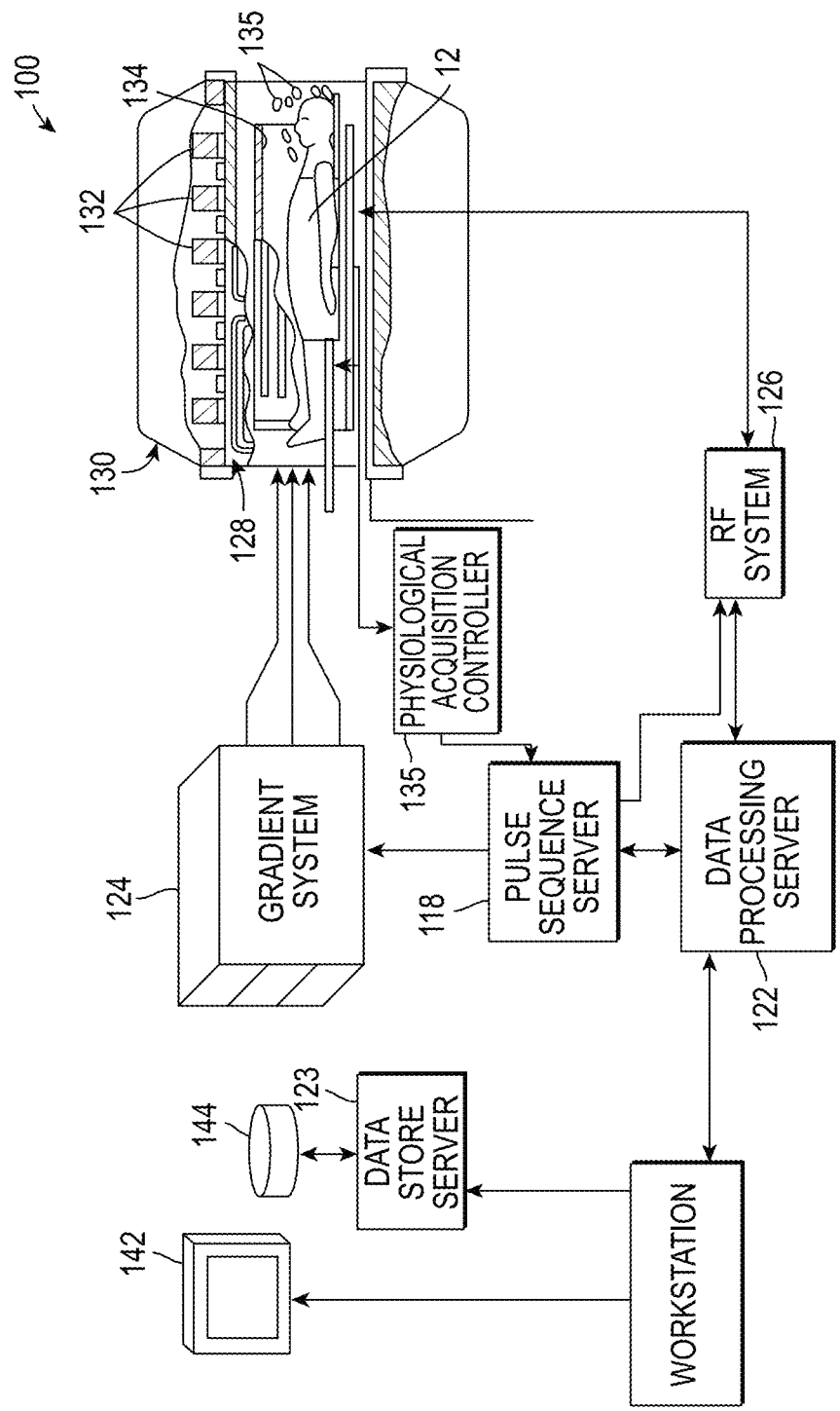
FIG. 1 shows a schematic block diagram of an exemplary MSRI system configured to carry out the MRSI techniques according to one or more embodiments.

FIG. 1 shows a schematic block diagram of an exemplary MSRI system 100 configured to carry out the MRSI techniques described herein. The MRSI system 100 includes a workstation 110, a pulse sequence server 118, a data processing server 122, a data store server 123, a gradient system 124, an RF system 126, and an MRI chamber 130. The MRI chamber 130 is a known instrument configured to receive a human patient 12, and includes gradient coils 132 and RF coils 135.

In general, the MRSI system 100 operates to apply a series of RF pulses and magnetic gradients to a patient subject 12 within the chamber 130. The MRSI system 100 is configured to record responsive RF signals generated by the reaction of the nuclei in the subject 12 to the applied RF pulses and magnetic gradients. In accordance with the embodiments described herein, the MRSI system 100 is configured to generate MRSI imaging data and displays using density-weighted concentric ring k-space trajectories using simultaneous multi-slice acceleration. The workstation 100 is configured to display representations of metabolite spacing in tissue of the subject 12 based on the MRSI imaging data.

The workstation 110 includes at least one programmable processing device, which executes computer instructions stored in a non-transitory storage medium, to carry out the operations attributed to the workstation 110 herein. The workstation 110 may take other forms. The operations of the workstation 110 may be carried out by other devices, such as portable computing devices and the like. In this embodiment, the workstation 110 includes a processor that is a commercially available programmable machine running a commercially available operating system. The workstation 110 includes an operator interface that enables scan prescriptions to be entered into the MRSI system 100, as is known in the art. The scan prescriptions dictate the sequence of operations of, for example, the gradient system 124 and the RF system 126 to generate pulses shown in FIG. 3, discussed further below.

The workstation 110 is coupled to each the pulse sequence server 118, the data processing server 122, and the data store server 123. It will be appreciated that the use of the term server does not imply that the functions of such servers must be carried out on different computing devices. One or more of the servers 118, 122, 123 may be implemented on the same computing device, and/or on the workstation 110. In any event, the workstation 110 and each server 118, 122 and 123 are operably coupled to communicate with each other.

The pulse sequence server 118 is a processing unit configured to operate the gradient system 124 and a radiofrequency ("RF") system 126 in response to instructions downloaded from the workstation 110. The data processing server 120 is configured to carry out the various functions that convert raw MRS signals to MRSI imaging data. The data store server 123 is configured to store the MRSI imaging data for use by the workstation 110 for enabling display.

The gradient system 124 is an electrical device that is operably coupled to provide gradient waveforms to excite gradient coils 132 within the MRI chamber 130 to produce magnetic field gradients $G_x$, $G_y$, and $G_z$ on the volume of interest ("VOI"). In this description, the x-y plane describes the horizontal plane, and the z-direction is the vertical direction. The gradient system 124 is configured to generate the gradient waveforms responsive to gradient signals received from the pulse sequence server 118. The gradient coils 132 are electromagnetic coils disposed throughout the chamber 130 that are configured collectively to generate magnetic gradients $G_x$, $G_y$ and $G_z$ in three dimensions, e.g., x, y and z dimensions, in response to the gradient waveforms received from the gradient system 124. Suitable pulse sequence servers, gradient systems and corresponding coil configurations generally capable of generating magnetic field gradients $G_x$, $G_y$ and $G_z$ within an MRSI chamber responsive to instructions from a workstation are known in the art and may take multiple forms. For example, suitable pulse sequence servers, gradient systems and gradient coils can be found in a Siemens Prisma 3-Tesla MRI scanner.

The RF system 126 is a circuit that both generates RF pulses on RF coils 134, 135 within the chamber 130, and receives echo RF signals therefrom, which constitute the MRS raw output signal, which is sometimes referred to as the acquired MRS signal or FID signal. The RF coil 134 is a whole body coil used in many MRI chambers 130, usually for transmitting RF pulses from the RF system 126. The RF coils 135 constitute an array of coils, in this example, at least 20, for receiving RF echo signals that constitute the acquired MRSI information. The RF coils 134 in this embodiment are shown disposed about the head of the subject 12, as would be necessary for a brain MRSI operation. In other embodiments, the RF coils 135 may be disposed proximate to and around another portion of the subject 12, such as the abdomen for kidney MRSI scans, or the chest for heart MRSI scans.

The RF system 126 is configured to generate excitation waveforms and provide the excitation waveforms to the RF coil 134 and/or coils 135 to perform the prescribed magnetic resonance RF pulse sequence. The RF system 126 thus includes a transmitter that is responsive to the scan prescription and direction from the pulse sequence server 118 to produce RF pulses of the desired frequency, phase and pulse amplitude waveform.

Accordingly, the RF coils 135 are configured to detect responsive MRS signals. As discussed above, the RF coils 135 can be disposed about any portion of the human subject 12 within the chamber. In the example of FIG. 1, the RF coils 135 are disposed about the head of the subject 12, which may be used to acquire MRS data about the brain. The RF system 126 is further configured to amplify, demodulate, filter and digitize the received MRS raw signal under direction of commands produced by the pulse sequence server 118. To this end, the RF system 126 includes a plurality of RF receiver channels. Each RF receiver channel includes an RF amplifier that amplifies the MR signal received by the coil to which it is connected and a detector that detects and digitizes the I and Q quadrature components of the received MRS signal. The magnitude of the received MR signal may thus be determined at any sampled point by the square root of the sum of the squares of the I and Q components.

In some embodiments, the pulse sequence server 118 also optionally receives patient data from a physiological acquisition controller, not shown, but which is known in the art. The physiological acquisition controller 136 receives signals from a number of different sensors connected to the patient subject 12, such as ECG signals from electrodes or respiratory signals from a bellows. Such signals can be used by the pulse sequence server 118 to synchronize, or "gate," the performance of the scan with the subject's respiration or heartbeat.

As discussed above, the data processing server 122 is configured to receive the digitized MRS signal samples produced by the RF system 126. The data processing server 122 operates in response to instructions downloaded from the workstation 110 to receive the real-time MR data and provide buffer storage such that no data is lost by data overrun. In some scans that require information derived from acquired MRS data to control the further performance of the scan, the data processing server 122 is programmed to produce such information and convey it to the pulse sequence server 118. For example, during prescans MRS data is acquired and used to calibrate the pulse sequence performed by the pulse sequence server 118. Also, navigator signals may be acquired during a scan and used to adjust operating parameters of the RF system 126 or gradient system 124, for example, to control the view order in which k-space is sampled. In all these examples, the data processing server 122 acquires MR data and processes it in real-time to produce information that is used to control the scan.

Figure 7:
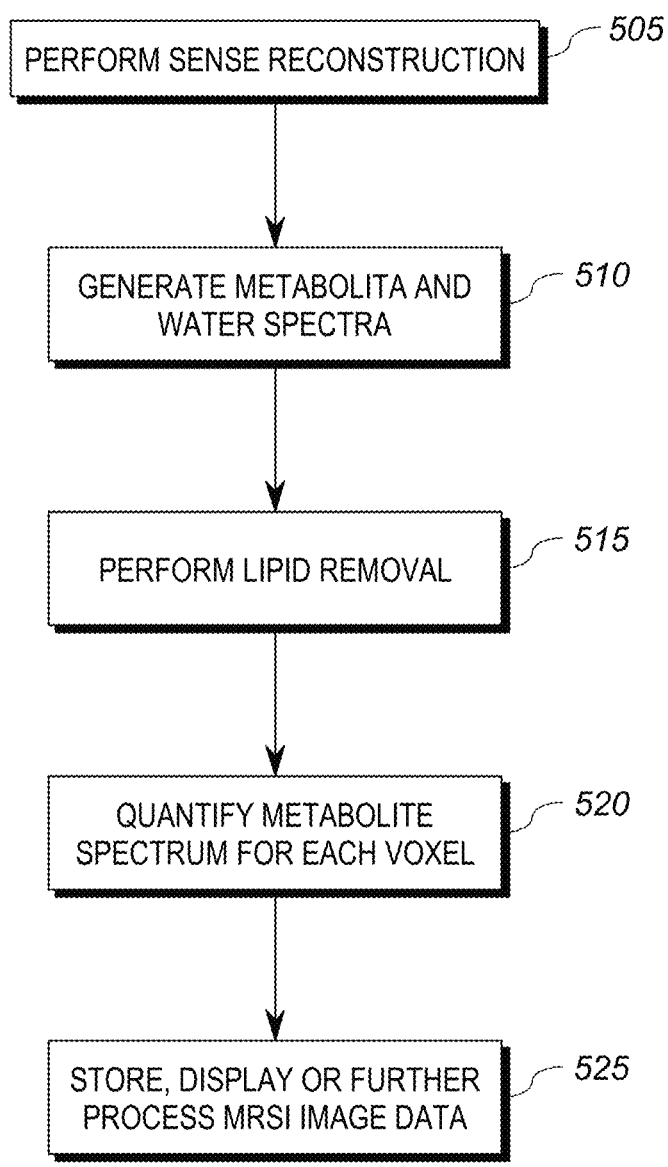
FIG. 7 shows a flow diagram of post processing steps that are performed by the data processing server of the MRSI system of FIG. 1.

One primary function of the data processing server 122 however, is to generate the MRSI image data based on the digital MRS signals received from the RF system 126. The data processing server 122 is configured to processes received digital MRS signals in accordance with instructions downloaded from the workstation 110. FIG. 7 shows a flowchart of processing operations of the data processing server 122. As will be discussed further below, such processing may include, for example: Fourier transformation of raw k-space MRS data to produce three-dimensional images; the application of filters to a reconstructed image, and the calculation of metabolite spectra.

Images reconstructed by the data processing server 122 are conveyed back to the workstation 110 where they are stored, for example, in the data store server 123. Real-time images are stored in a data base memory cache (not shown) from which they may be output to operator display 112 or a display 142 that is located near the chamber 130 for use by attending physicians. Batch mode images or selected real time images are stored in a host database on disc storage 144. When such images have been reconstructed and transferred to storage, the data processing server 122 notifies the data store server 123 on the workstation 110. The workstation 110 may be used by an operator to archive the images, produce films, or send the images via a network to other facilities.

In general, this embodiment includes a method of performing magnetic resonance spectroscopic imaging (MRSI) to measure neurochemical profiles over larger regions noninvasively. The method includes transmitting a multi-slice excitation pulse through tissue of the subject 12 (see FIG. 1), the multi-slice excitation pulse configured to generate multi-slice MRSI signals representative of characteristics of the tissue. In general, this pulse is generated by a pulse generator in the sequence server 118, which is then transmitted via a transmission coil 134 to the tissue, which in this case is brain tissue. Further detail regarding the multi-slice excitation pulse is provided below.

In accordance with at least some embodiments, the MSRI system 100 establishes readout magnetic gradients to form MRSI signals. A plurality of slice-encoding blips are sequentially produced, as will be described further below. As part of the acquisition, the array of sensor coils 135 disposed about the tissue (e.g. around but external to the brain) capture the generated multi-slice MRSI signals, in the presence of the magnetic gradients. The magnetic gradients are configured to execute a density weighted, concentric ring trajectory k-space acquisition, as will be discussed below.

The data acquisition server 120 and the data processing server 122 receive and process the generated multi-slice MRSI signals. The data processing server 122 in the exemplary arrangement disclosed herein reconstructs imaging data for a plurality of tissue slices based on the received density weighted concentric ring trajectory k-space MRSI signals. Details regarding such reconstruction are provided further below.

The MRI workstation 110 may then cause a display of a representation of the imaging data on the display 142 as will be discussed below. Various novel aspects and variants of the method are discussed herebelow.

Figure 2:
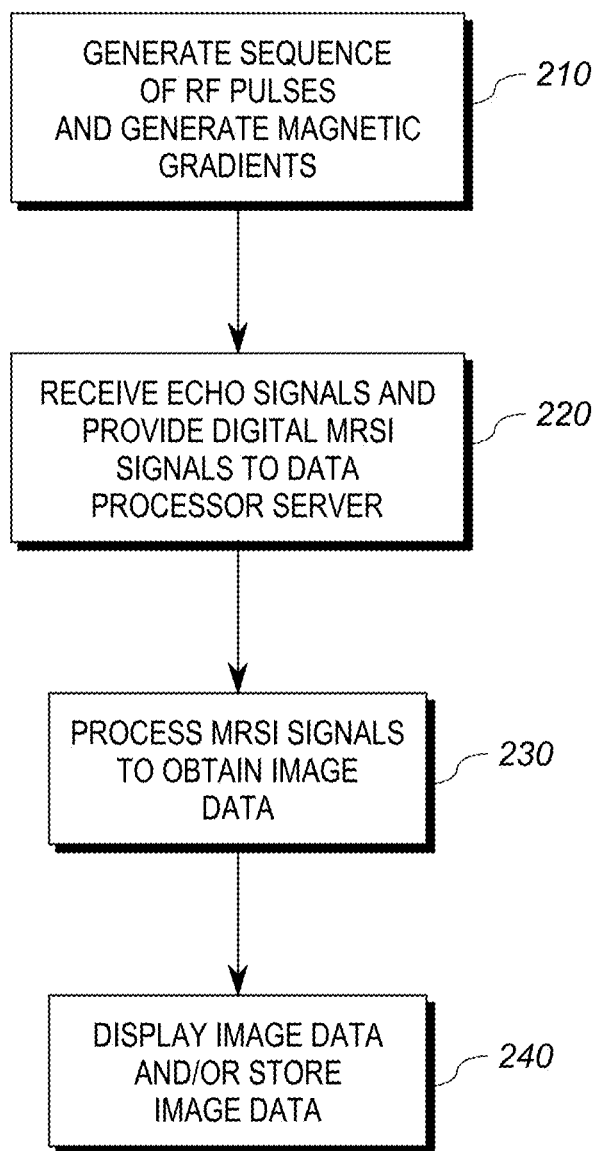
FIG. 2 shows a flow diagram of a method of obtaining MRSI spectral data that may be implemented through the MRSI system of FIG. 1.

FIG. 2 shows a flow diagram of a method of obtaining MRSI spectral data that may be implemented through the MRSI system 100 of FIG. 1. In step 210, the pulse sequence server 118 causes the RF system 126 to generate a sequence of pulses, and caused the gradient system 124 to generate signals to cause the gradient coils 132 to generate magnetic field gradients $G_x$, $G_y$ and $G_z$. An exemplary sequence 321 of RF pulses and magnetic gradients are shown, by way of example, in FIG. 3. In general, the pulse sequence server 118 in this embodiment causes the gradients and RF pulses to be generated to enable acquisition of a concentric ring k-space trajectory on multiple x-y plane slices. By way of example, FIG. 5 shows a representation of a three-slice k-space trajectory 450 having a first slice 452, a second slice 454 and a third slice 456. The three slices 452, 454, and 456 are excited simultaneously in the embodiments described herein using the multi-slice excitation RF pulse, as mentioned above. Further detail regarding the multi-slice excitation pulse is discussed further below in connection with FIGS. 6a and 6b.

Thereafter in step 220, the RF system 126 receives the raw MRSI signals as sensed by all of the RF coils 135. As is known in the art, each raw MRSI signal is an echo signal that results from the sequence of RF pulses and magnetic gradients applied in step 210. In the embodiment described herein, the MRSI signal preferably includes both metabolite and water spectral information corresponding to the three slices 452, 454 and 456 shown in FIG. 5. The RF coils 135 sense the MRSI signal and convey the MRSI signal to the RF system 126. The RF system 126 using filtering and other known methods to generate a MRSI signals from the raw MRSI signals received from all of the coils 135. The RF system 126 further samples the MRSI signal to generate a digitized MRSI signal and provides the digitized MRSI signal to the data processing server 122.

In step 230, the data processing server 122 receives the digitized MRSI signals and reconstructs imaging data for a plurality of tissue slices in accordance with the density weighted concentric ring trajectory acquisition. The data processing server 122 reconstructs the image data to provide various spectral information for a plurality of voxels that correspond to areas on the three slices 452, 454 and 456. The data processing server 122 makes the acquired MRSI imaging data available for the work station 110.

In accordance with one embodiment of the present invention, steps 210 and 220 can be performed twice—once for water spectra and once for a combination of water and metabolite spectra. As will be discussed further below, this allows the water spectra and metabolite spectra to be processed for images separately. In such a case, step 230 generates image data to provide both water spectra and metabolite spectra.

Thereafter, in step 240, the work station can display and/or store the acquired MRSI imaging data. Various methods of displaying acquired MRSI imaging data are known, and discussed below in connection with several exemplary MRSI scans.

Figure 3:
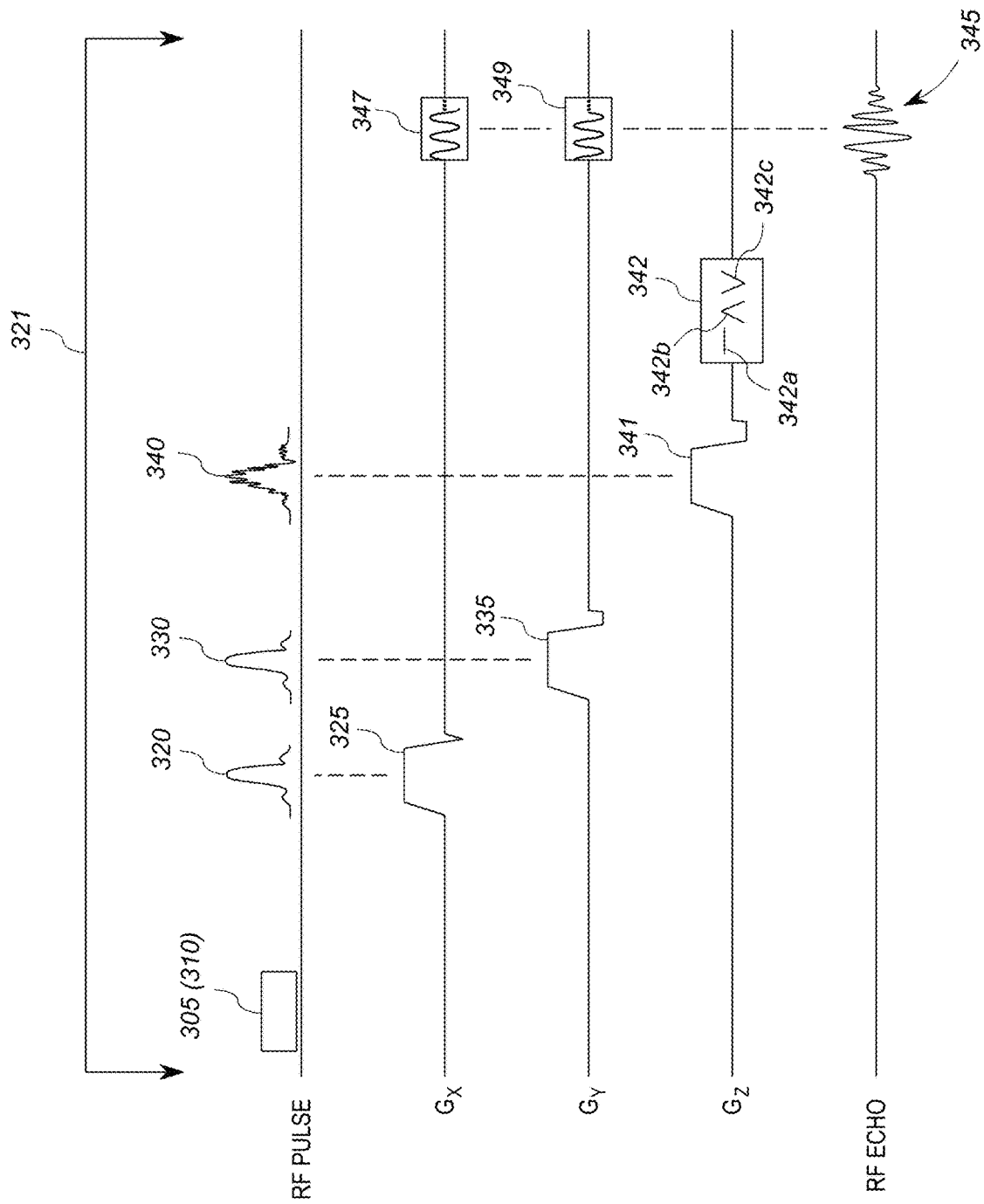
FIG. 3 shows a RF pulse sequence and corresponding gradient timing diagram used in carrying out the method of FIG. 2.

FIG. 3 shows a timing diagram of sequence 321 RF pulses and magnetic gradients applied repeatedly in step 210 of the method of FIG. 2. In this embodiment, the RF system 126 and gradient system 124 generate the sequence 321 of RF pulses and gradients for each of a plurality of N rings on each of a plurality of M slices. In other words, the ring sequence 321 of FIG. 3 is performed N×M times to generate a set of multi-slice concentric ring k-space trajectory FID signals (e.g. trajectory 450 of FIG. 5). In this example, M=3, as indicated by the slices 452, 454, and 456 of FIG. 5. Furthermore, in this embodiment, the value of N=32. In other words, each of the slices 452, 454 and 456 has 32 concentric rings. It will be appreciated that the numbers N and M may vary to suit the particular implementation needs.

Moreover, in this embodiment, the entire sequence 321 is repeated another N×M times to generate a second set of FID signals to obtain different spectral information. To generate the two sets of FID or MRSI signals, the sequence 321 includes a first of two spectral resonance RF pulses 305, 310 for the first set, and includes the second of the two spectral resonance RF pulses 305, 310 for the second set. The reason for two sets of MRSI signals is to preserve water spectra and metabolite spectra. As discussed above, the water spectra can be used later for frequency and phase alignment, eddy current correction, and as the internal concentration reference. To this end, the two pulses 305, 310 invert the upfield and downfield spectral resonances. Details regarding this known technique, albeit applied in a single slice context, are discussed in Emir U. E., Burns B., Chiew M., Jezzard P., Thomas M. A., "Non-water-suppressed short-echo-time magnetic resonance spectroscopic imaging using a concentric ring k-space trajectory." *NMR in Biomedicine* 2017, which is incorporated herein by reference.

Figure 4A:
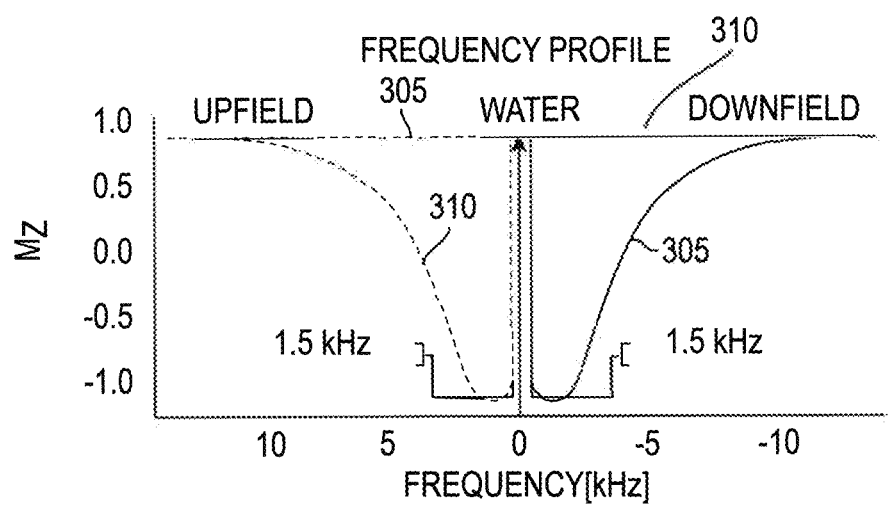
FIG. 4a shows a frequency spectrum of first and second pulses of the pulse sequence of FIG. 3.
Figure 4B:
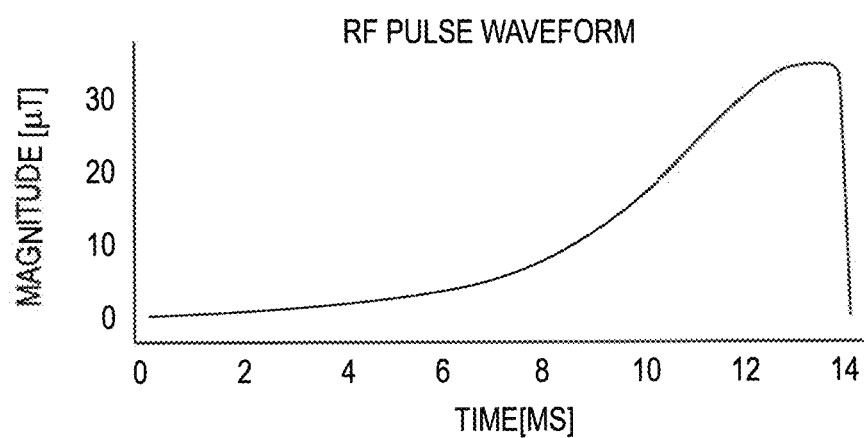
FIG. 4b shows a magnitude timing diagram of the first and second pulses of FIG. 3.

In general, however, each of the first and second pulses 305, 310 have a frequency profile based on water, except that one is frequency inverted. The frequency profile of the first and second pulses 305, 310 is shown in FIG. 4. The pulse sequence 321 of FIG. 3 is first performed N×M times with the first pulse 305 to create the first set of MRSI signals, and then subsequently performed N×M times with the second pulse 310 to generate the second set of MRSI signals.

In addition to one of the two pulses 305, 310, the ring sequence 321 includes RF pulses 320, 330 and 340, and corresponding magnetic gradients 325, 335, 341, 342 and 347, 349. Each ring sequence 321 generates an FID signal 345 corresponding to an nth ring on an mth slice, referred to below as ring $R_{m,n}$.

In each single ring sequence 321 for a ring $R_{m,n}$, the RF system 126 generates first the select one of the pulses 305, 310. Thereafter, the RF system 126 generates an excitation pulse 320, while the gradient system 124 causes the gradient coils 132 to generate a slice selection Gx magnetic gradient 325 as shown in FIG. 3. After the excitation pulse 320, the RF system 126 generates a pulse 330. At the same time, the gradient system 124 generates slice selection gradient 335 in y direction 335. The slice selection gradient 335 corresponds to the mth slice (452, 454, or 456)

Figure 6A:
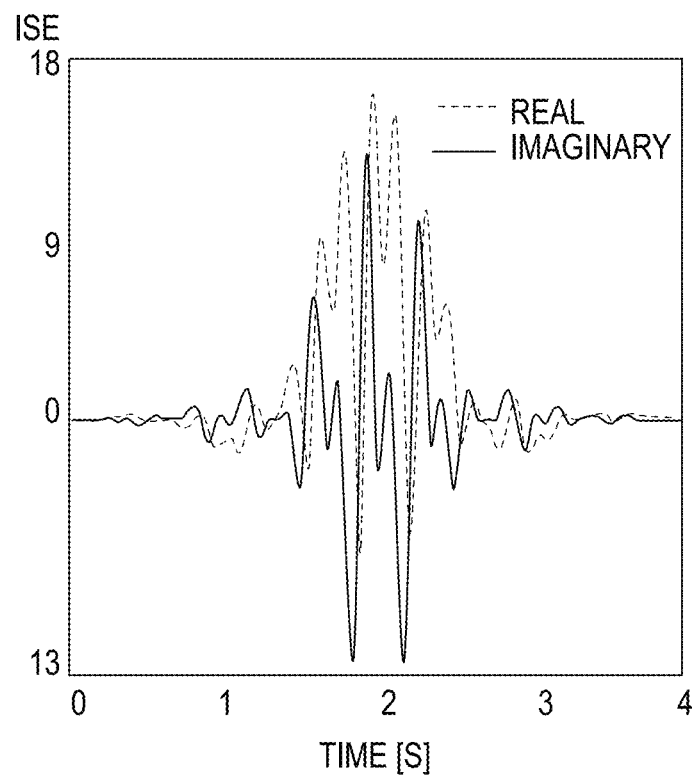
FIG. 6a shows a multi-slice excitation pulse that may be used in the pulse sequence of FIG. 3.
Figure 6B:
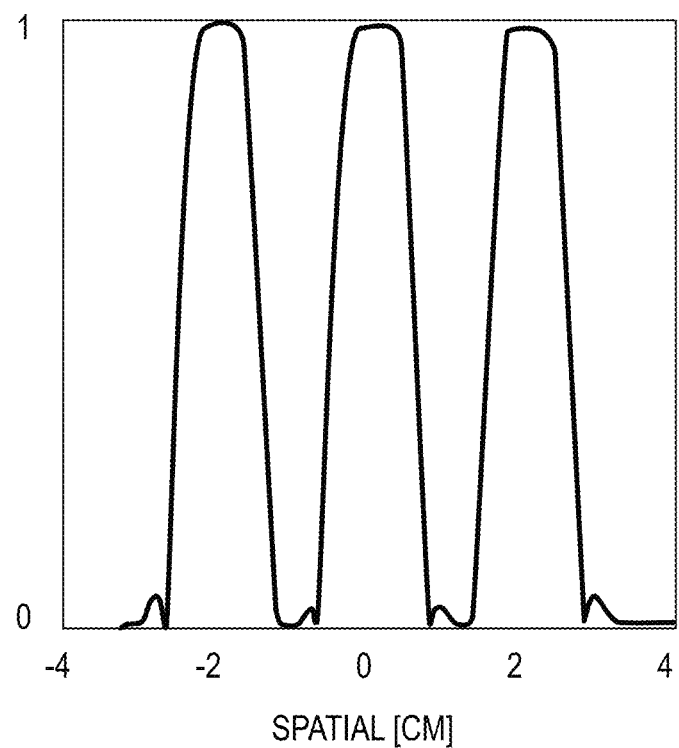

Thereafter, the RF system 126 generates a multiband excitation pulse 340. In the slice-accelerated multiband discussed herein, the number of simultaneously excited slices dictates the number of bands required in the multiband excitation pulse 340. In the exemplary embodiment described herein, where m=3, the multiband excitation pulse has three bands. In this case, the slice spacing is 2 cm, and the slice width is approximately 1 cm, as shown in FIG. 6b. The multibands of the excitation pulse 340 may be formed from select frequency bands or select phase bands.

Because multiple slice-selective pulses are applied simultaneously, the multiband approach could quickly run into a peak power limitation. To avoid this issue, the multiband excitation pulse 340 of the embodiment described herein uses an optimal phase modulation method to reduce multiband pulse peak power as proposed by Wong et al. resulting in a $\sqrt{N}$ (instead of N) times of increase of peak $B_1$ compared with that of single band pulse. See Wong E., "Optimized Phase Schedules for Minimizing Peak RF Power in Simultaneous Multi-Slice RF Excitation Pulses." *Proceedings of the 20th Annual Meeting of ISMRM* 20 (2012).

In one embodiment, the peak $B_1$ for 4 ms single band pulse is 8.22 µT (per the prior art method of single slice excitation), while that of 4-ms multiband pulse is 18.38 µT. The spectral bandwidth for each band is 1.55 KHz for both single band and multiband pulses. FIG. 6a illustrates the phase-modulated multi-band RF pulse 340 in the time domain. FIG. 6b shows the localized excitation pulses in the three slices 452, 454, 456 resulting from the application of the pulse 340.

Contemporaneous with the multi-band excitation pulse 340, the gradient system 124 causes phase-encoding $G_z$ magnetic gradient 341 to be applied by the gradient coils 132. With the multiband pulse 340 and the gradient 341, in this example, three 10 mm slices can be excited simultaneously with a 20 mm distance between center of adjacent slices.

Thereafter, a z-gradient blip 342 is used to encode the slice m. The z-gradient blip is a select one of the z-gradient blips 342a, 342b, and 342c, depending on whether m corresponds to slice 452, 454 or 456. Generally, the use of z-gradient blips 342 decreases the coil geometry factor. As will be discussed below, the z-gradient blips 342a, 342b, and 342c, are interleaved such that they sequence through and repeat every third run of the sequence 321, and hence the value m is interleaved. This technique is generally discussed in Setsompop K, Gagoski B A, Polimeni J R, Witzel T, Wedeen V J, Wald L L., "Blipped-controlled aliasing in parallel imaging for simultaneous multislice echo planar imaging with reduced g-factor penalty." *Magnetic Resonance in Medicine* (2012).

The echo pulse 345 for the ring $R_{m,n}$ is then acquired in k-space using gradient signals 347, 349. In this embodiment, the gradient signal 347 is a sine wave and the gradient signal 349 is a cosine wave, each configured to have 512 periods during the length of the echo signal 345. The gradient signals 347, 349 are configure to correspond to the concentric ring n. The FID signal for the ring $R_{m,n}$ thus results from the echo pulse 345 detected by the RF coils subject to the gradients 347, 349.

As discussed above, the ring sequence 321 is repeated 32 times for each slice m. As mentioned above, however, each consecutive sequence is performed for a different slice 452, 454, 456. Hence, the corresponding z-gradient blips in this embodiment are 0, ⅙ cycle/cm, and −⅙ cycle/cm, repeating every three rings. This results in three spatial interleaves (number of spatial interleaves, $N_{si}$=3) of 32 DW concentric rings (number of rings, $N_{ring}$=32) with different phase modulation and aliasing patterns in three slices. The middle slice remains unmodulated, the top slice experiences an additional (0, 120, −120) phase cycle, and the bottom slice experiences an additional (0, −120, 120) phase cycle of every three rings. The gradients 347, 349 are further configure such that the ring spacing in the concentric ring trajectory increases as a function of distance from a center of the ring trajectory.

Unlike the purely spatial shift in phase encoding direction in CAIPIRINHA and blipped-CAIPI, the aliasing patterns of top and bottom slices are spreading out because the Fourier transform of the phase modulation is no longer a spatial Dirac function, which are similar to the aliasing patterns shown by Chu, A., Noll, D. C. "Coil compression in simultaneous multislice functional MRI with concentric ring slice-GRAPPA and SENSE". *Magnetic Resonance in Medicine* (2016) doi: 10.1002/mrm.26032.

Thus, in this embodiment, the concentric ring acquisition is the $k_x$-$k_y$ trajectory composed of 96 distinct concentric rings with 160 equidistant points on each ring. To this end, a series or frequency encoding x gradients and phase encoding y gradients are applied a series of times to acquire each point on each ring. Within one repetition time (TR) duration, only one ring will be acquired and repeated for 512 times for spectral encoding.

It will be appreciated that the density weighting acquisition method is used to determine the radii because the non-uniform k-space sampling density allows effective windowing during acquisition instead of post-processing, providing higher efficiency, as discussed in Greiser A, Von Kienlin M. Efficient k-Space Sampling by Density-Weighted Phase-Encoding. Magnetic Resonance in Medicine 2003. A Hanning-window sampling density is selected due to its good compromise between sensitivity and localization. The Hanning-window is given by:

$$w(k) = \frac{\Delta x}{2}\left(1 + \cos\left(\frac{2\pi k \Delta x}{\alpha}\right)\right)$$

where $\Delta x$ is the nominal spatial resolution, and $\alpha$ is the parameter adjusting the effective spatial resolution by modulating the width of the SRF main lobe. The $\alpha$ is set to 1 for the maximum radius of $1/(2\Delta x)$.

Referring again specifically to FIG. 3, after the N×M (e.g. 96) repetitions of the ring sequence 321 using the pulse 305, the entire process is repeated using the pulse 310. This provides MRSI or FID signals that can be combined to generate water spectra, and differentiated to generate metabolite spectra.

As discussed above, the MRSI signals are sampled by the RF system 126. The RF system 126 provides the sampled MRSI signals to the data processing server 122. The data processing server 122 then acquires MRSI image data from the digitized MRSI signals using the technique shown in FIG. 7.

Referring to FIG. 7, the data processing server 122 in step 505 first an FFT-based reconstruction of the image from the MRSI signals. In this embodiment of step 505, the data processing server 122 performs a SENSE reconstruction of the multiband MRSI data. In one embodiment, NUFFT gridding is performed without using any post-hoc density compensation because density weighting method relies on different sampling density of different k-space locations. To this end, sensitivity maps for SENSE reconstruction were estimated from the single-band calibration data based on the adaptive filtering method to optimize the SNR, as discussed in Walsh, D. O., Gmitro, A. F., Marcellin, M. W., "Adaptive reconstruction of phased array MR imagery." *Magnetic Resonance in Medicine* (2000) doi: 10.1002/(SICI)1522-2594(200005)43:5<682::AID-MRM10>3.0.CO;2-G. The NUFFT (Fessler, J. A., Sutton, B. P., "Nonuniform fast Fourier transforms using min-max interpolation." *IEEE Transactions on Signal Processing* (2003) doi: 10.1109/TSP.2002.80700523) and SMS (discussed in Chu, et al., supra) toolboxes can be used to do the non-cartesian SENSE reconstruction of single band and multiband MRSI data.

Thereafter, in step 510, the data processing server 122 generates the water and metabolite spectra. To this end, upfield and downfield single-shot metabolite-cycled FIDs in each voxel are frequency and phase corrected. Then, the FIDs are summed to generate water spectra and subtracted to generate metabolite spectra, as discussed in Emir, U. E., Burns, B., Chiew, M., Jezzard, P., Thomas, M. A., "Non-water-suppressed short-echo-time magnetic resonance spectroscopic imaging using a concentric ring k-space trajectory." *NMR in Biomedicine* (2017) doi: 10.1002/nbm.3714. In this embodiment, the residual water peak of metabolite spectra is removed using the Hankel-Lanczos singular value decomposition (HLSVD) algorithm. See Cabanes, E., Confort-Gouny, S., Le Fur, Y., Simond, G., Cozzone, P. J., "Optimization of residual water signal removal by HLSVD on simulated short echo time proton MR spectra of the human brain." *Journal of Magnetic Resonance* (2001) doi: 10.1006/jmre.2001.2318.

In step 515, the data processing server 122 performs lipid removal on the voxel data. In particular, lipid removal in the three slice example is performed on all three slices using a lipid-basis penalty algorithm. The lipid basis can be generated from the top slice subcutaneous lipid area, the mask of which is hand-drawn based on the observed contrast between the brain and non-brain tissue in the water MRSI images. In one embodiment, an L2-penalty iterative reconstruction with a regularization parameter of $10^{-1}$ can be applied to remove lipid from metabolite MRSI assuming that metabolite spectra from brain and lipid spectra from lipid mask were orthogonal. See Bilgic B, Chatnuntawech I, Fan A P, et al. Fast image reconstruction with L2-regularization. Journal of Magnetic Resonance Imaging 2014 doi: 10.1002/jmri.24365. The voxels processed within the brain region can then be passed to metabolite analysis.

To this end, in step 520, the data processing server 122 quantifies the metabolite spectrum for each voxel. Specifically, the LCModel package was used to quantify the metabolite spectrum for each MRSI voxel. The model spectra of alanine (Ala), aspartate (Asp), ascorbate/vitamin C (Asc), glycerophosphocholine (GPC), phosphocholine (PC), Cr, phosphocreatine (PCr), GABA, glucose, glutamine (Gln), glutamate (Glu), glutathione (GSH), lactate (Lac), myo-Inositol (myo-Ins), NAA, N-acetylaspartylglutamate (NAAG), and taurine (Tau) were generated based on previously reported chemical shifts and coupling constants by the GAMMA/PyGAMMA simulation library of VeSPA (Versatile Simulation, Pulses and Analysis) according to a density matrix formalism. Simulations were performed using the same RF pulses and sequence timings as those on the 3 T system in use. Five LCModel-simulated macromolecule resonances were included in the analysis at the following spectral positions: 0.91, 1.21, 1.43, 1.67, and 1.95 ppm.

In step 525, the various acquired MRSI image data can be stored, selectively displayed or otherwise used.

Non-Water Suppressed Metabolite Cycling MRSI Acquisition

One enhancement to this embodiment is the preservation of water spectra and metabolite spectra (i.e. "non-water-suppressed metabolite-cycling MRSI"), discussed above. In experiments that implemented the method of FIG. 2, non-water-suppressed metabolite-cycling MRSI was acquired using parameters described in Emir et al., supra, which is incorporated herein by reference. Briefly, the metabolite-cycling MRSI acquisition was achieved by the inversion of the upfield and downfield (Ndirections=2) spectral resonances (pulses 305, 310 of FIG. 3) before localization pulse 320 with a gap of 9.6 ms so that water spectra (addition of two spectra) and metabolite spectra (subtraction of two spectra) can be kept simultaneously. The water spectra would later be used for frequency and phase alignment, eddy current correction, and as the internal concentration reference, such as in step 510 of FIG. 7. The inversion pulses 305, 310 include a hyperbolic secant pulse $HS_{1/2}$ and tanh/tan pulse [HS-½, R=10, 0.9 Tp; tanh/tan, R=100, 0.1 Tp], providing a sharp transition band of 80 Hz $$\left(-0.95 < \frac{M_z}{M_0} < 0.95\right)$$

and a broad inversion band of 820 Hz $$\left(-1 < \frac{M_z}{M_0} < -0.95\right).$$

Experimental Data

The above methods were applied experimentally to demonstrate results. Phantom and in-vivo scans were acquired using a Siemens Prisma 3-Tesla (Siemens, Germany) scanner and a 20-channel head array receive coil. T1-weighted MP-RAGE images (TR=2200 ms, TE=2.48 ms, TI=900 ms, flip angle=8°, 176 transverse slices, 0.9×0.9×1 mm³) were acquired for MRSI VOI placement. GRESHIM (gradient-echo shimming) was used for $B_0$ shimming.

Phantom Acquisitions

At the beginning of all experiments, single-band MRSI data were acquired separately from the same locations as the multiband MRSI for calculation of coil sensitivities and quality comparison analysis between multiband and single band analysis. The single band acquisition used the same acquisition scheme as multiband without having the z-blips gradients and the multiband excitation pulse. The multiband MRSI acquisition was tested on two phantoms. The first phantom was the American College of Radiology (ACR) structural phantom. The second phantom measurement was from a multi-compartment MRS phantom containing six hollow spheres filled with different concentrations of NAA and Creatine (Cr). The NAA and Cr distributions measured by single-band and multiband acquisition schemes were used to evaluate multiband sequence performance. The FOV of MRSI acquisition was 240 mm×240 mm. The STEAM localization (TR=1 s, TE=14 ms, and a mixing time (TM)=32 ms) was 160 mm×160×10 mm. To cover the 48×48 grid, 32 DW concentric rings resulting in an individual voxel size of 0.25 mL were acquired with three spatial interleaves for single band and three z-gradient blips for multiband acquisition. The multiband acquisition was acquired with six average (Navg=6) resulted in an acquisition duration of 19.2 min (Navg×Nrings×Nsi×$T_R$×Ndirections=1152 s) whereas single band acquisition of three slices with one average was completed in 9.6 min (Nslc×Nrings×Nsi×$T_R$×Ndirections=576 s).

In Vivo Acquisition

In-vivo acquisition was performed with the identical parameters. Only in-plane dimension of the STEAM localization was reduced to 80 mm×110 mm so that only the top slice extended to the subcutaneous lipid layer while the middle slice and bottom slice cover as big brain region as possible.

Post-Processing

Post processing for the experiment was carried out as discussed above in connection with FIG. 7.

Structural Similarity Index (SSIM) Analysis

In this study, we explore to use the Structural Similarity Index (SSIM) was used to measure the similarity of generated water and metabolite images of multiband acquisition against the single band ones. Conventional voxel-wise coefficient variance (CV) between multiband and single band water images and metabolite maps were also calculated to assess the deviation of multiband from single band data.

Results

Slice Unaliasing Evaluation of Multi-Band MRSI Acquisition

Figure 8:
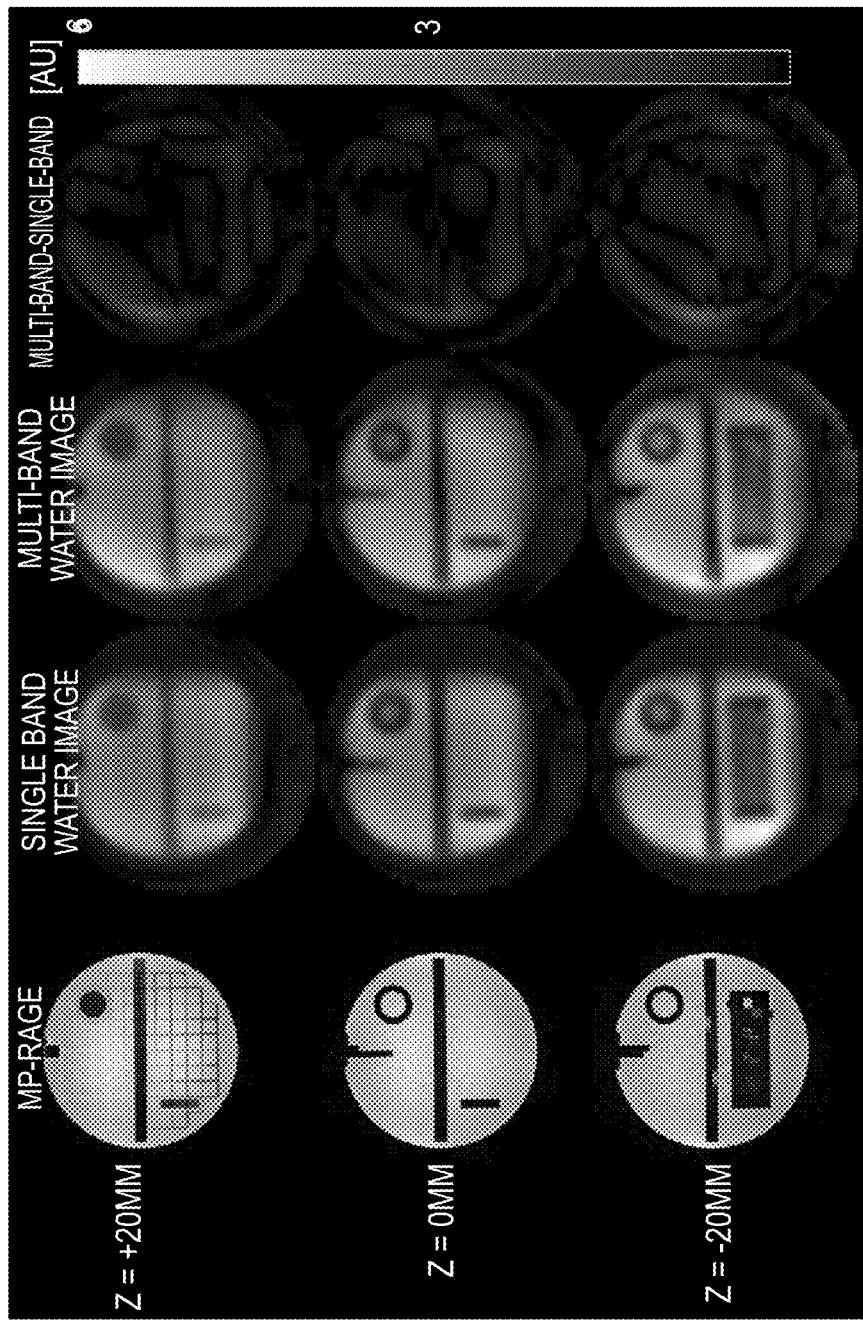
FIG. 8 shows a g-factor map of the acquisition and reconstruction steps carried out in an exemplary MRSI operation according to an embodiment described herein.

The performance of slice unaliasing of multi-band MRSI acquisition was evaluated based on the reconstructed water images (magnitude of first-time point of FID in each voxel) of ACR phantom as illustrated in FIG. 8. The left panel of FIG. 8 shows the g-factor map of the proposed acquisition and reconstruction steps. The reconstructions with regularization allowed mean g-factors of less than 1. Although the final resolution of the images generated from FIDs of multi- and single-band acquisitions was poorer than the MP-RAGE images (0.25 mL versus 0.001 mL), the non-water-suppressed metabolite-cycling MRSI and its reconstruction generated a spectroscopic image with structural information similar to that of MPRAGE. The artifacts originating from proposed unaliasing procedure mainly appeared near the edge, while they were not evident in inner regions. Distinct components of each slice are not visibly contaminating other slices, such as the grids, wedges with different lengths, and hole arrays, demonstrating the capability of SENSE unaliasing of blipped concentric ring trajectories.

Metabolites Quantification Accuracy of Multi-Band MRSI Acquisition—Phantom MRSI

Figure 9:
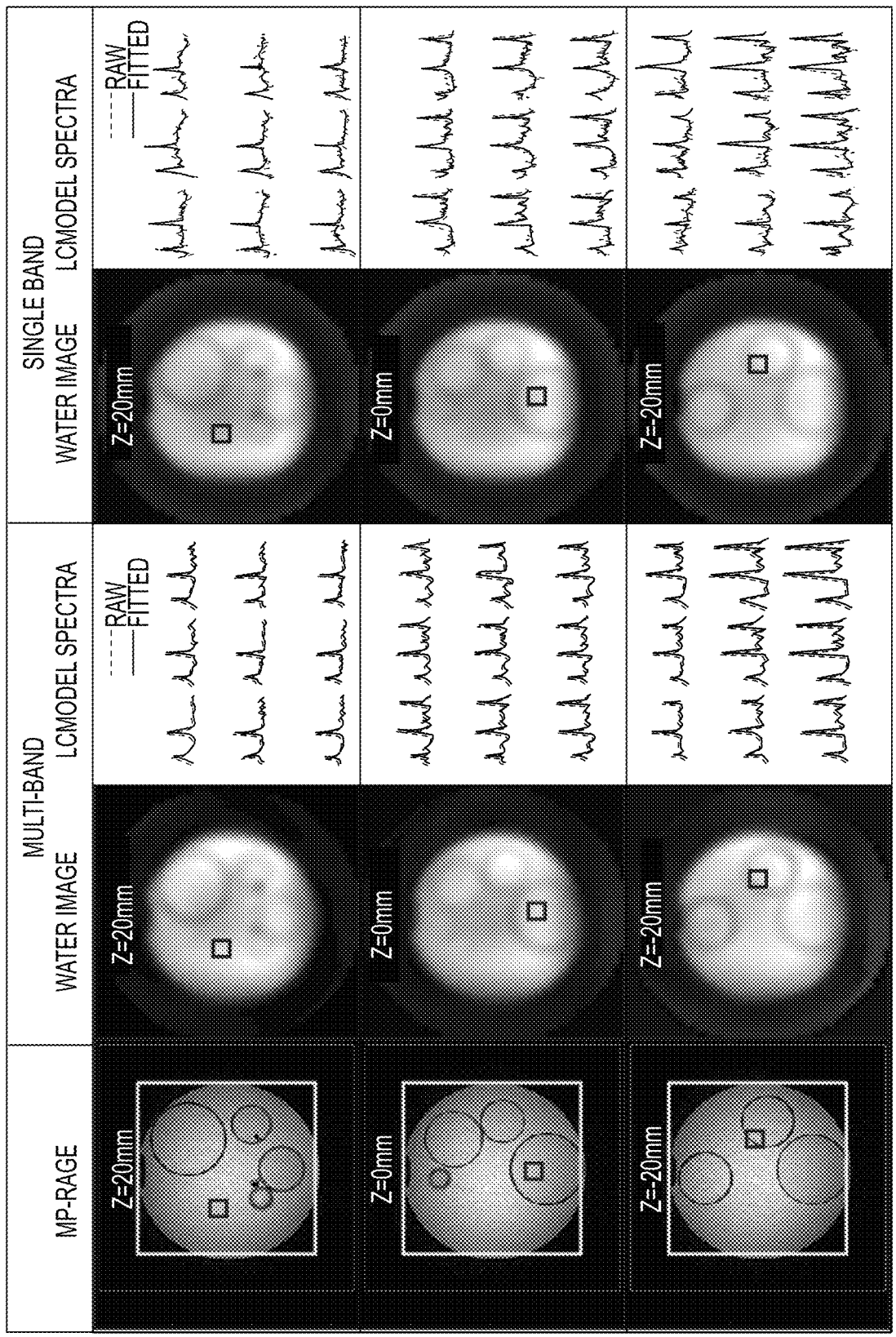
FIG. 9 shows results of an exemplary process of the method disclosed herein for a multi-compartment MRS phantom scan.
Figure 10:
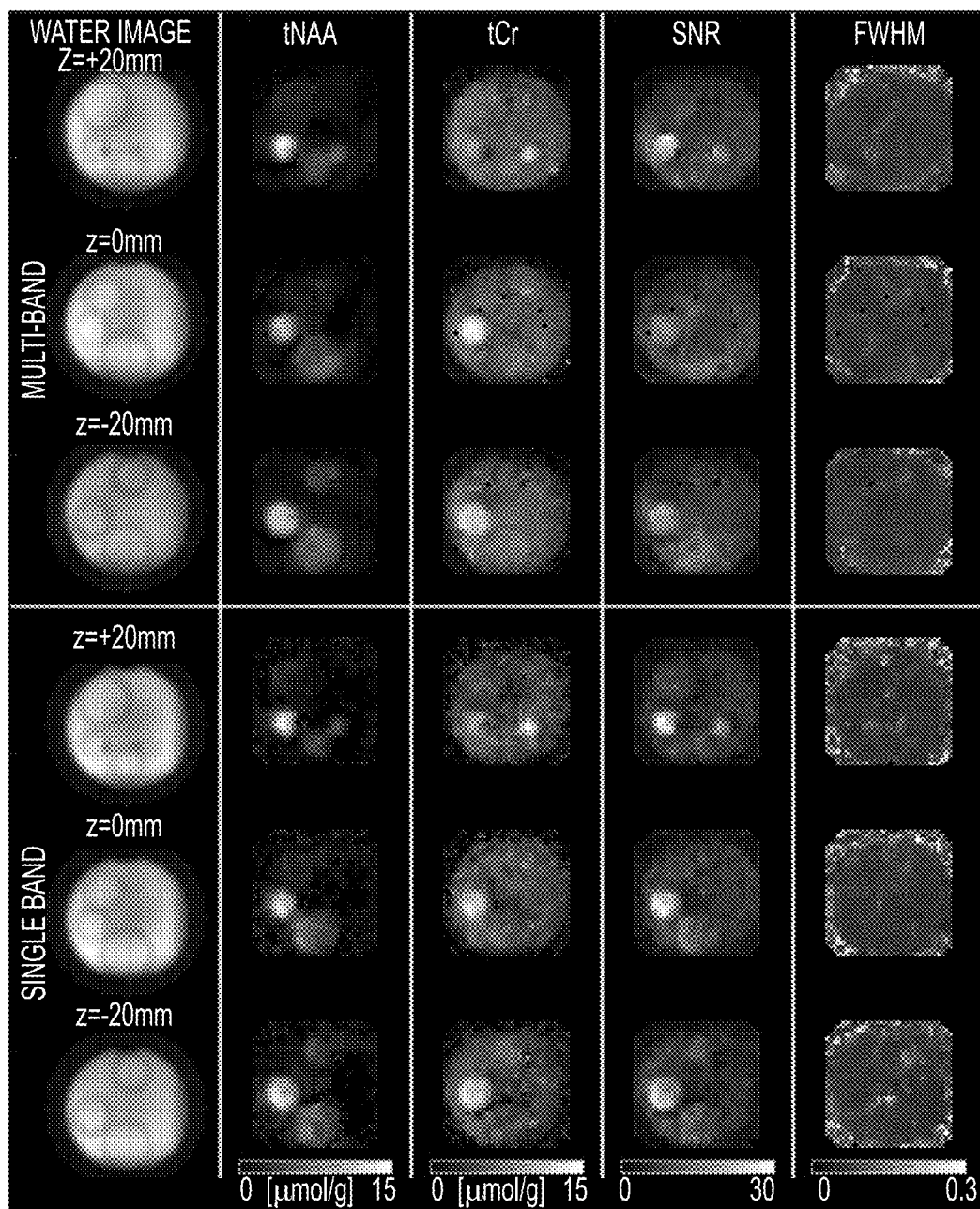
FIG. 10 shows structural similar index (SSIM) maps of tNAA maps from a three-slice MRSI scan performed in accordance with the technique of FIG. 2.

FIG. 9 shows results from the multi-compartment MRS phantom, including representative spectra from single and multi-band in a 3×3 grid marked on the reconstructed water images. The accuracy of metabolites quantification of multi-band MRSI acquisition was estimated based on the comparison against the single-band MRSI results. FIG. 9 also shows MP-RAGE, water, NAA, Cr and corresponding LCModel quality metrics, SNR, and FWHM maps. The multiband SNR has been divided by the square root of the Navg of multiband, 6, to compensate the Navg difference between single-band and multiband acquisitions. The similarity between generated metabolites images is visually distinct. SSIM and CV analyses further corroborated this similarity. As shown in FIG. 10, the SSIM maps of tNAA maps from three slices demonstrated very high similarity indexes in the compartments where NAA presents. The mean SSIM of NAA in the hollow spheres was higher than 0.83, corresponding to a coefficient of variance of less than %30. However, Cr maps showed homogeneous distributions of SSIM in three slices since the presence of Cr in the container.

Figure 11:
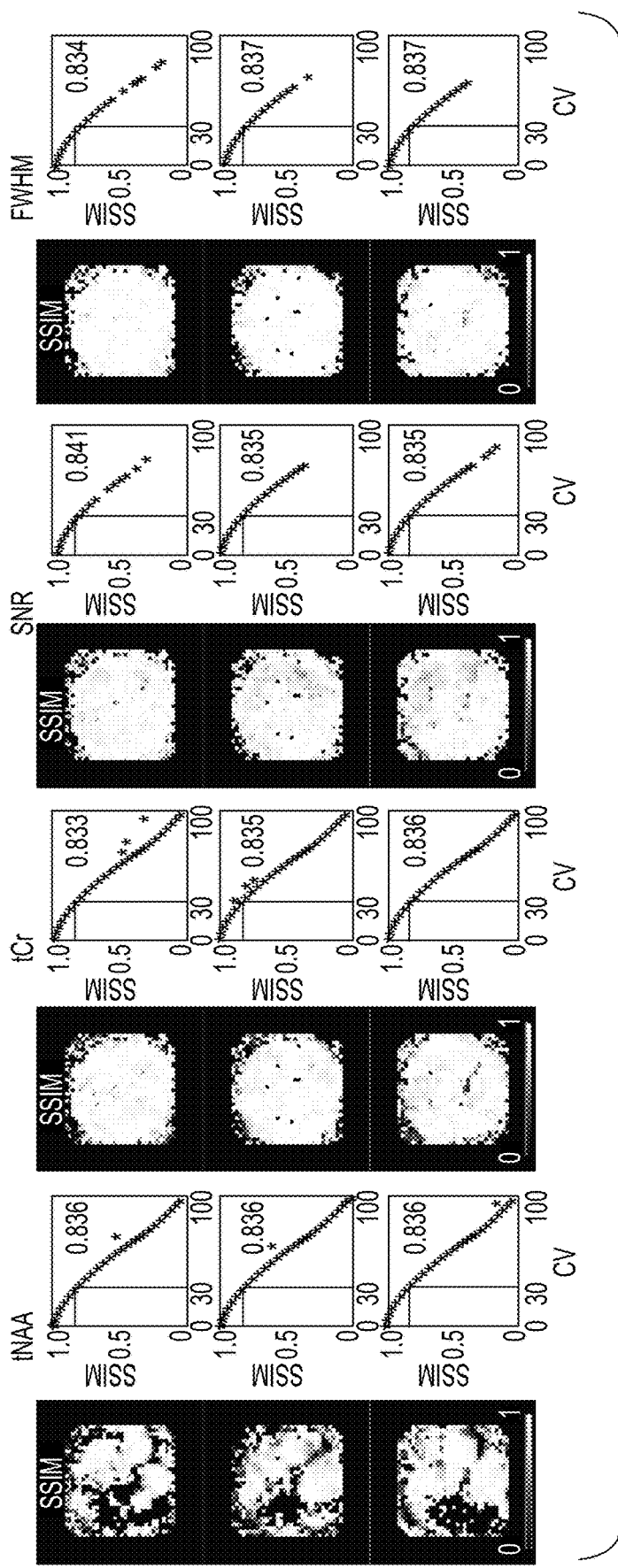
FIG. 11 shows the relationship between SSIM and coefficient variance (CV) for the SSIM maps of FIG. 10.

Similarly, FWHM and SNR maps also have high SSIM values, indicating the minimal spectra quality degradation caused by multiband acceleration. The relationship between SSIM and CV is illustrated in FIG. 11. The SSIM values corresponding to a CV of 30 are marked on the plot. The numbers of voxels for each slice with a CV of less than 30% were listed in Table 1.

Metabolites Quantification Accuracy of Multi-Band MRSI Acquisition—In Vivo MRSI

Figure 12:
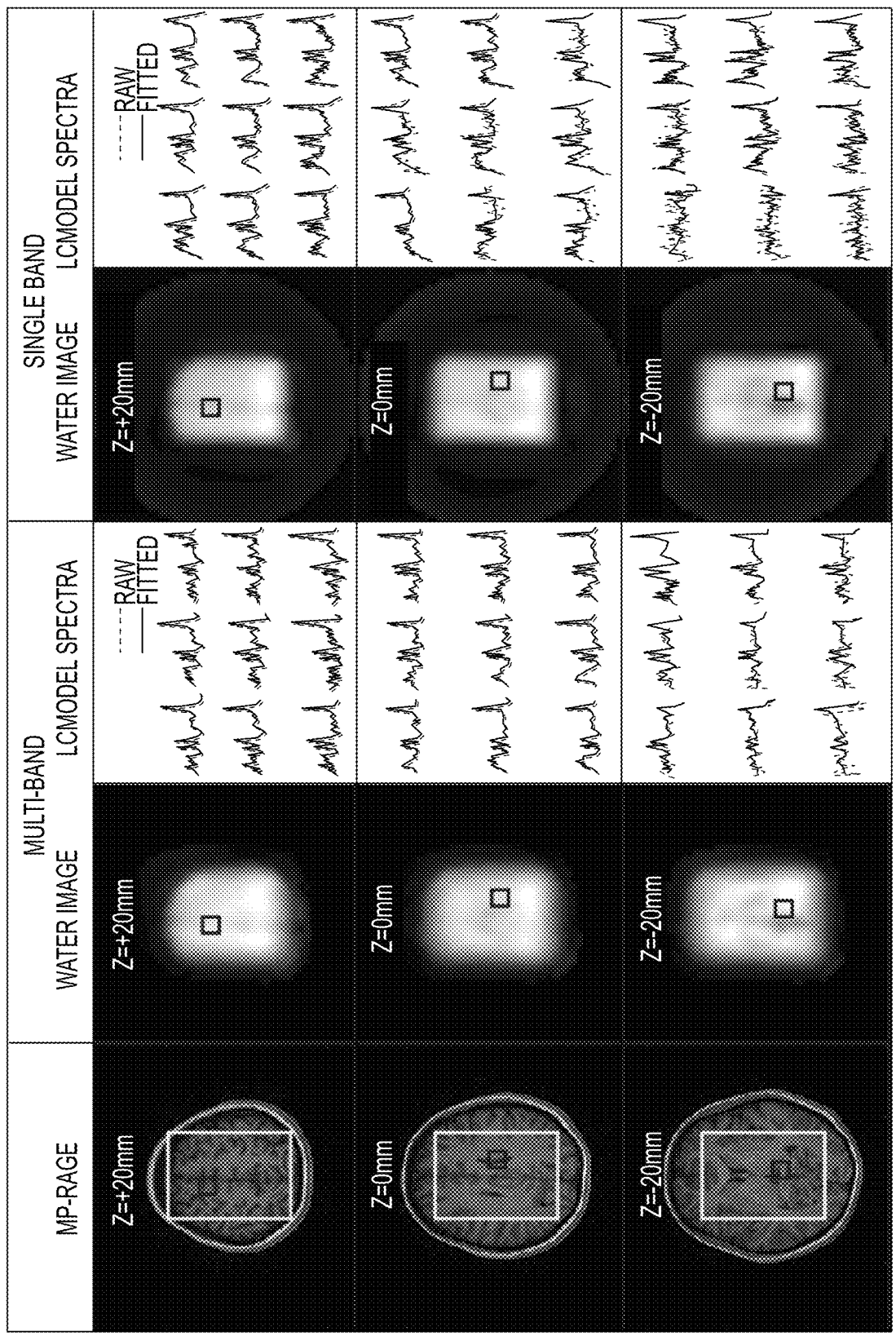
FIG. 12 shows representative single- and multi-band spectra from an exemplary implementation of the methods described herein on an in vivo scan.

FIG. 12 shows the representative single- and multi-band spectra from a volunteer. As illustrated on a 3×3 grid from three slices, metabolite spectra with LCModel fits from multi-band MRSI resulted in similar spectral features of single-band MRSI. For example, ventricular CSF showed low levels of all metabolite signals (slice z=−20 mm), and white matter spectra showed an increase in tCho/tCr ratio compared to gray matter spectra (slice z=0).

Figure 13:
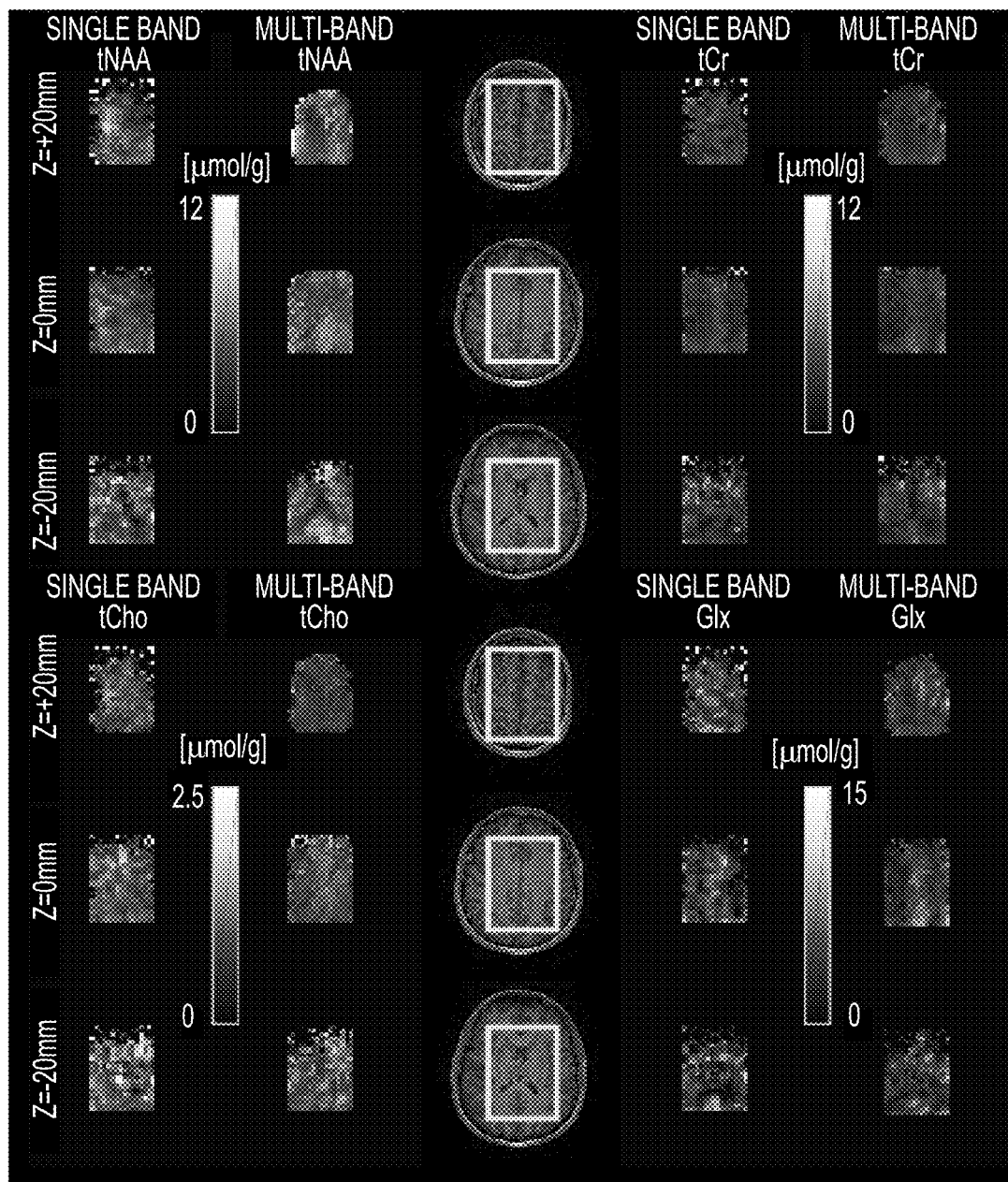
FIG. 13 shows single- and multi-band tNAA, tCr, and Glx maps for the in vivo scan.
Figure 14:
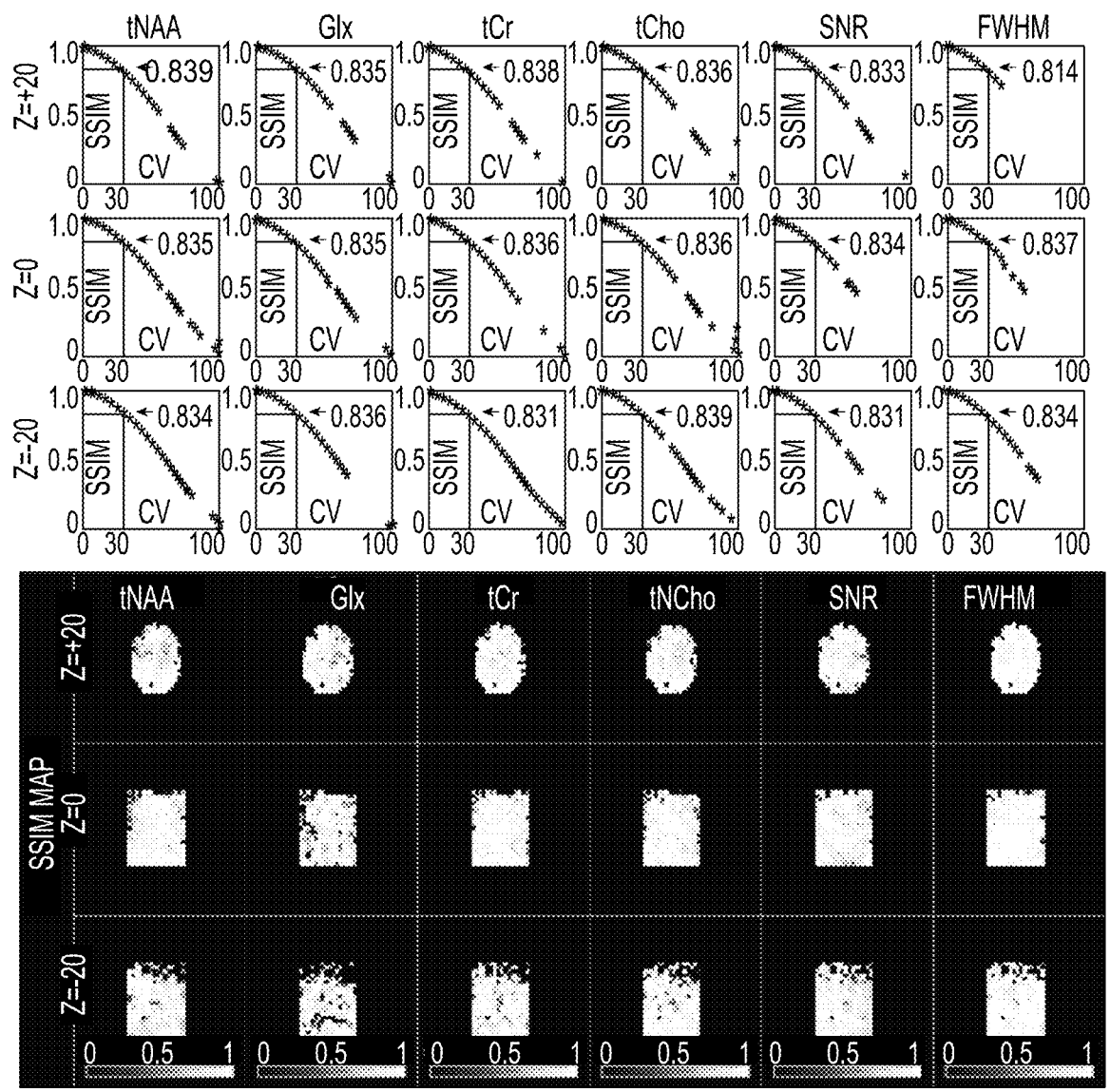
FIG. 14 shows the relationship between SSIM and coefficient variance (CV) for in vivo scan.

For the multi-band MRSI acquisition with a resolution of 0.25 mL, the achieved in vivo spectral quality allowed reliable quantification of major brain metabolites with a CRLB of less than 50% using LCModel analysis. Concentration distributions of metabolites quantified were in good agreement with the single-band acquisition and previously reported values acquired from the same brain locations, and revealed significant variations between different brain tissues. As shown in FIG. 13 the lack of metabolite signals in the region of ventricles resulted in low concentration estimation for both single- and multi-band tNAA, tCr, and Glx maps of the bottom slices (z=−20 mm). The contrast of gray matter and white matter was also evident on tCr and Glx maps of the superior slices (z=0 and +20 mm). In agreement with the phantom experiment, SSIM and CV analyses resulted in similar findings. Most voxels in three slices resulted in SSIM value higher than 0.83 corresponding to a CV of 30%, as shown in FIG. 14.

In this work, we demonstrated a non-water suppressed multi-band MRSI acquisition using DW-CRT. The results from structural and the multi-compartment metabolite phantom show single and multi-band acquisition schemes produce similar quality spectra. In line with the phantom measurement, the in vivo results exhibited multi-band acquisition spectroscopic images of NAA, tCho, tCr, and Glx with an in-plane resolution of 5×5 mm$^2$ and a slice thickness of 10 mm. The metabolite concentration values measured using the short-TE MRSI of all slices for different tissues were consistent with the literature (see below).

Compared to the EPI base acceleration techniques, DW-CRT has been demonstrated to offer a substantial improvement in SNR (12). The present study further accelerates the DW-CRT with simultaneous multi-slice excitation combined with SENSE parallel imaging technique. it had been demonstrated that z-blips using concentric rings result in less overlap and, therefore, a better g-factor. In line with this previous study, using SENSE resulted in an average g of less than 1 using z-blipped DW-concentric rings, Mark would you mind adding something here.

Structural and multi-compartment phantom experiment findings were further supported by in vivo experiments. In agreement with phantom experiments, multi and single-band DW-CRTs resulted in similar metabolite concentrations, SNRs FWHMs as estimated by LCModel and their distributions as determined by SSIM and CV analysis.

For the multi-band MRSI acquisition with a resolution of 0.25 mL, the achieved in vivo spectral quality allowed reliable quantification of primary brain metabolites with a CRLB of less than 50% using LCModel analysis. Concentration distributions of metabolites quantified in this study were in good agreement with previously reported values acquired from the same brain locations and revealed significant variations between brain tissues. tNAA and tCr have low values in the regions close to the skull, nasal cavity, and ventricles. Glx and tCr showed higher concentrations in the region of gray matter compared with white matter. In addition, we found elevated tCho, specifically tCho/tCr, in WM in comparison with GM.

There remain several limitations of the implemented methods. in this study, we chose to utilize STEAM localization with a penalty of two-fold signal loss compared with PRESS or semi-LASER since short TE values can easily be achieved with lower peak RF pulse powers, yielding a lower specific absorption rate (SAR). The use of the lipid penalty may also affect the quality of the absolute metabolite measures across the acquired region and reduce sensitivity to some metabolites. Using outer volume suppression pulses to suppress the lipid contamination during acquisition could make lipid removal unnecessary. This acquisition strategy should be explored in future studies.

It will be appreciated that the above discussed embodiments are merely illustrative, and that those of ordinary skill in the art may readily devise their own implementations and modifications that incorporate the principles of the invention fall within the spirit and scope thereof.

The invention claimed is:

1. A method of performing magnetic resonance spectroscopic imaging (MRSI) to measure neurochemical profiles over larger regions non-invasively, comprising:
   a) transmitting a multi-slice excitation pulse through tissue, the multi-slice excitation pulse configured to generate multi-slice MRSI signals;

b) performing density weighted concentric ring acquisition on the multi-slice MRSI signals;
c) receiving the generated multi-slice MRSI signals in a plurality of sensors disposed in various locations around the tissue;
d) reconstructing imaging data based on the acquired imaging signals;
e) displaying a representation of the imaging data.

2. The method of claim 1, wherein a ring spacing in the concentric ring trajectory increases as a function of distance from a center of the ring trajectory.

3. The method of claim 1, further comprising obtaining sensitivity data for each of the plurality of sensors and using the sensitivity data in step d).

4. The method of claim 3, wherein the plurality of sensors comprises at least 20 sensors.

5. The method of claim 1, further comprising repeating steps a) and b) for each of a plurality of concentric rings in a volume of interest.

6. The method of claim 5, wherein step b) further comprises applying a slice selective magnetic gradient blip.

7. The method of claim 6, wherein each of a plurality of repetitions of step b) comprises applying a different slice selective magnetic gradient blip.

8. A method of performing magnetic resonance spectroscopic imaging (MRSI) to measure neurochemical profiles over larger regions non-invasively, comprising:
a) transmitting a multi-slice excitation pulse through tissue, the multi-slice excitation pulse configured to generate multi-slice MRSI signals;
b) performing density weighted concentric ring acquisition on the multi-slice MRSI signals;
c) receiving the generated multi-slice MRSI signals in a plurality of sensors disposed in various locations around the tissue;
d) reconstructing imaging data based on the acquired imaging signals;
e) displaying a representation of the imaging data, and
wherein step a) further comprises using first and second pulses to invert the upfield and downfield spectral resonances to preserve water spectra and metabolite spectra.

9. The method of claim 8, wherein step d) further comprises generating water spectra and metabolite spectra as part of the acquired imaging data.

10. The method of claim 8, further comprising repeating steps a) and b) for each of a plurality of concentric rings in a volume of interest.

11. The method of claim 10, wherein each of a plurality of repetitions of step b) comprises applying a different slice selective magnetic gradient blip.

12. The method of claim 8, wherein a ring spacing in the concentric ring trajectory increases as a function of distance from a center of the ring trajectory.

13. The method of claim 12, further comprising repeating steps a) and b) for each of a plurality of concentric rings in a volume of interest.

14. The method of claim 12, wherein each of a plurality of repetitions of step b) comprises applying a different slice selective magnetic gradient blip.

15. A method of performing magnetic resonance spectroscopic imaging (MRSI) to measure neurochemical profiles over larger regions non-invasively, comprising:
a) transmitting a multi-slice excitation pulse through tissue, the multi-slice excitation pulse configured to generate multi-slice MRSI signals;
b) performing density weighted concentric ring acquisition on the multi-slice MRSI signals;
c) receiving the generated multi-slice MRSI signals in a plurality of sensors disposed in various locations around the tissue;
d) reconstructing imaging data based on the acquired imaging signals;
e) displaying a representation of the imaging data; and
wherein step a) further comprises generating the multi-slice excitation pulse using phase modulation to create the multi-slice excitation.

16. The method of claim 15, wherein each phase of the phase modulation corresponds to a corresponding slice, and wherein the phase modulation has three modulated phases.

17. The method of claim 15, wherein step d) further comprises generating water spectra and metabolite spectra as part of the acquired imaging data.

18. The method of claim 17, wherein a ring spacing in the concentric ring trajectory increases as a function of distance from a center of the ring trajectory.

19. The method of claim 15, wherein a ring spacing in the concentric ring trajectory increases as a function of distance from a center of the ring trajectory.

20. The method of claim 15, wherein step b) further comprises applying a slice selective magnetic gradient blip.

* * * * *